United States Patent [19]
Ain et al.

[11] Patent Number: 6,015,376
[45] Date of Patent: Jan. 18, 2000

[54] DNA SEQUENCE CORRESPONDING TO THE MINIMAL ESSENTIAL PROMOTER OF THE HUMAN SODIUM-IODIDE SYMPORTER (HNIS)

[75] Inventors: Kenneth Bruce Ain; Gopalakrishnan Venkataraman, both of Lexington, Ky.

[73] Assignee: University of Kentucky Research Foundation, Lexington, Ky.

[21] Appl. No.: 09/006,186

[22] Filed: Jan. 13, 1998

[51] Int. Cl.$^7$ .......................... C07H 21/02; C07H 21/04; C12Q 1/68

[52] U.S. Cl. .............................. 586/23.1; 536/24.3; 435/6

[58] Field of Search .................................. 536/23.1, 24.3; 435/6; 935/76, 77, 78

[56] References Cited

U.S. PATENT DOCUMENTS 5,739,284  4/1998  Hediger et al. .......................... 530/350

OTHER PUBLICATIONS

Venkataraman et al., Thyroid 8 (1):63–69 (Jan. 1998).

Cloning of the Human Sodium Iodide Symporter, P.A. Smanik, Q. Liu, T.L. Furminger, K. Ryu, S. Xing, E.L. Mazzaferri, S.M. Jhiang, Biochemical and Biophysical Research Communications, Article No. 1358, pp. 226, 339–345 (1996).

Cloning and Characterization of the Thyroid Iodide Transporter, G. Dal, O. Levy, N. Carrasco, Nature, vol. 379, pp. 458–459, Feb. 1, 1996.

Regulation by Thyroid–Stimulating Hormone of Sodium/Iodide Symporter Gene Expression and Protein Levels in FRTL–5 Cells, T. Kogai, T. Endo, T. Saito, A. Miyazaki, A. Kawaguchi, T. Onaya, Endocrinology, vol. 138, No. 6, pp. 2227–2232 (1997).

Expression, Exon–Intron Organization, and Chromosome Mapping of the Human Sodium Iodide Symporter, P.A. Smanik, K. Ryu, K.S. Theil, E.L. Mazzaferri, S.M. Jhiang, Endocrinology, vol. 138, No. 8, pp. 3555–3558 (1997).

Promoter Characterization of the Rat Na$^+$/1$^-$ Symporter Gene, Biochemical and Biophysical Research Communications, Article No. RC977432, Q. Tong, K. Ryu, S.M. Jhiang, pp. 239, 34–41 (1997).

Thyroid Transcription Factor–1 Activates the Promoter Activity of Rat Thryroid Na$^+$/1$^-$ Symporter Gene, T. Endo, M. Kaneshige, M. Nakazato, M. Ohmori, N. Harii, T. Onaya, Molecular Endocrinology (1997), vol. 11, pp. 1747–1755.

*Primary Examiner*—W. Gary Jones
*Assistant Examiner*—Ethan Whisenant
*Attorney, Agent, or Firm*—McDermott, Will & Emery

[57] ABSTRACT

Elucidation of the regulation of human sodium-iodide symporter (hNIS) gene expression is critical to understanding its effects on iodide concentration abilities of thyroid and thyroid carcinomas. A 1.2 kb portion of the 5'-flanking region of the hNIS gene has been isolated and characterized, and the nucleotide sequence for the minimal essential promoter of the hNIS gene is shown in FIG. 1. Transient transfections with chimeric luciferase-reporter constructs into a differentiated human thyroid cell line, KAT-50, as well as non-thyroidal cells, define an active promoter having tissue-specificity. KAT-50 cells expressed hNIS mRNA and were capable of thyrotropin-responsive iodide uptake in vitro.

10 Claims, 2 Drawing Sheets

```
                                                                  tagctgg
gattacaggcatgtgccaccacgcctcgctaatattagtatttttcatacagacaagatc
tcactatgttgctcagggtagtctcgaattctgggactcaaatgatcctcccacttcagc
ctcccaaagtgctgggattacaggcataagccatcatgcccggcctctgacgctgtttct      -1501 ttcaaccccaggatttcagattccaccagcttatggagaagggaaccaagttcgagatg
cgtgattgcccagaaagttggaggctgagctgagacttgaacccagagaccagaacctcc
agaggtcaaagtcctcctcctgggtccccagagaagggccctgagatgacagctcgttg
gtcctcatggaagcgtgacccccccagtagactttctcccacacccaaccttggtttcct
catctatatgatagggacaagccagactctacctccctggtggtcatggtctccgcttat     -1201 tcgggttcataaccttaaaggcccctcgcaccacctcagtgagccatttatgcctggcac
                      ↓C
agggccaactctcagtgcatatctgcaaaggaaccaatgaatgaatgaatgaagtgacaa
                                  ↓B
atgaataaaggaataaatgaatgaggcacttatcatgtaccaggctttcgttaccacgtc
ccatttattcctctgaggcagggtctattttatccttgttacagatggggaaactaaggc
                      ↓A
ccagggaggagcaaagtcttccccaagtatgtacccactcagaacttgagctctgaatgt     -0901 ctcccacccagcttagcccaagagcggggttcagtgatgcccacccctaaggctctaga
gaaaggggtaggcccacatgccagtttgggggtggtaaagccaggtaagttttctttat
gggtcccctgaaaccctgaaagtgaacccagtcctgcatgaaagtgagctccccatagc
tcaaggtattcaagcacaatacggctttgagtgctgaagcaggctgtgcaggcttggata
gtgacatgccctctctgagcctcaatttccccacctgtcaacagcagacagtgacagctg     -0601 tgatcaggggatcacagtgcatggggatggtgggtgcatggggatggaggggcatttgg
gagccctccccgataccaccccctgcagccaccagatagcctgtcctggcctgtctgtc
ccagtccagggctgaaagggtgcgggtcctgcccgcccctaggtctggaggcggagtcgc
                                                       ↓VA2
ggtgacccgggagcccaataaatctgcaacccacaatcacgagctgctcccgtaagcccc
    ↓VA1         ↓SJ      ↓
aaggcgacctccagctgtcagcgctgagcacagcgcccagggagagggacagacagccgg     -0301 ctgcatgggacagcggaacccagagtgagaggggaggtggcaggacagacagacagcagg
ggcggacgcagagacagacagcggggacaggaggccgacacggacatcgacagcccata
gattcctaacccagggagccccggcccctctcgccgcttccaccccagacggagcgggg
acaggctgccgagcatcctcccacccgccctccccgtcctgcctcctcggccctgccag
cttccccgcttgagcacgcagggcgtccgaggacgcgctgggcctccgcacccgccctc     -0001

ATGGAGGCCGTGGAGACCGGGGAACGGCCCACCTTCGGAGCCTGGGACTACGGGGTCTTT
```

SEQ ID NO: 1

Figure 1 and# DNA SEQUENCE CORRESPONDING TO THE MINIMAL ESSENTIAL PROMOTER OF THE HUMAN SODIUM-IODIDE SYMPORTER (HNIS)

STATEMENT OF GOVERNMENT SUPPORT

The present invention was funded in part under Grant CA58935 of the National Cancer Institute. The Government may have certain rights in the invention.

FIELD OF THE INVENTION

The present invention relates to the identification and elucidation of the nucleic acid structure of the human sodium-iodide symporter (hNIS) promoter. The invention also relates to characterization of the promoter in a differentiated human thyroid cell line, designated KAT-50.

BACKGROUND OF THE INVENTION

Thyroid follicular cells have the unique ability to concentrate iodide, which is organified and utilized for the synthesis of thyroid hormones. Transport of iodide across the follicular cell membrane, in concert with inward movement of $Na^+$ along its gradient, is an active process mediated by the tissue-specific sodium-iodide symporter (NIS).

A cDNA sequence for the rat NIS gene has been reported [Dai G., et al. (1996)] and the corresponding human cDNA sequence has been described [Smanik P., et al. (1996)]. The intronexon organization of the gene has also been reported recently [Smanik P., et al. (1997)].

A retention of the ability to concentrate iodide via the NIS in carcinoma cells derived from thyroid follicular cells provides an opportunity to destroy these cells with administered radioiodine. The efficacy of this approach relies upon adequate expression of functional NIS. Unfortunately, NIS expression in human thyroid carcinoma cells can be variable or absent, leaving some carcinomas untreatable by this approach. To understand the regulation of expression of the NIS gene in normal and malignant thyroid tissues, it is essential to understand regulation of transcription of this gene.

Smanik P., et al. (1996) describe cloning a cDNA encoding the hNIS protein and provide nucleotide sequence information for the coding region of this cDNA. A short (347 bp) untranslated region upstream of the translated region is also provided by these workers. Recently, Smanik P., et al. (1997) have described the exon-intron structure of the hNIS gene; however, this reference is unconcerned with the promoter region.

An extensive region upstream of the rat NIS gene has been described [Tong Q., et al., (1997), *Biochem. Biophys. Res. Comm.*, 239:34–41]. However, this region is not appreciably homologous with the promoter of the human NIS gene (vide infra). The authors report that a 90 bp region of the active rat promoter has a 75% homology with the hNIS gene. In our studies, the minimal active region of the rat NIS promoter of these workers has no more than 60% homology with the corresponding region of the human NIS promoter. Significantly, no thyroid-specific activity is demonstrated for the promoter of these authors. Some DNA sequence information pertaining to the promoter for the rat sodium-iodide symporter gene has also been described elsewhere [Endo T., et al., (1997), *Mol Endocrinol* 11 (11):1747].

An elucidation of the factors affecting regulation of expression of the human sodium-iodide symporter gene is critical to an understanding of its effects on iodide concentration in normal thyroid and thyroid carcinomas. Identification of the active promoter for the hNIS gene is expected to provide further insights that can lead to the development of new therapies for thyroid carcinomas using radioiodine.

SUMMARY OF THE INVENTION

The present invention is for the promoter for the human sodium-iodide symporter (hNIS) gene, as well as fragments and substantial homologs of the promoter that are effective in promoting transcription of the hNIS gene. The hNIS promoter is defined within the nucleotide sequence (SEQ ID NO: 1) shown in FIG. 1. Accordingly, an hNIS promoter of the invention has a high degree of homology, ranging upwards of 80%, with the hNIS promoter sequence shown in FIG. 1.

In a preferred embodiment, the promoter contains TTF1 (thyroid transcription factor-1), TTF2 (thyroid transcription factor-2), and PAX-8 transcription factor binding sites and may also contain SP1 transcription factor sites. As demonstrated herein, an effective promoter sequence is homologous to the nucleotide sequence shown in FIG. 1 (SEQ ID NO: 1) from about residue −1044 to about residue −348 from about residue 647 to about residue 1343 in SEQ ID NO: 1). Hence, a preferred embodiment is a promoter having a nucleotide sequence substantially identical with that shown in FIG. 1 from residue −1044 to residue −348 from about residue 647 to about residue 1343 in SEQ ID NO: 1). A further preferred embodiment is a promoter having a nucleotide sequence at least 80% homologous with that in FIG. 1 from about residue −1108 to residue −348 from about residue 583 to about residue 1343 in SEQ ID NO: 1). A particularly preferred promoter comprises the nucleotide sequence shown in FIG. 1 from about residue −1690 to about residue −348 from about residue 1 to about residue 1343 in SEQ ID NO: 1).

Another aspect of the invention is a DNA construct, e.g., an expression vector, comprising a promoter sequence of the invention operably linked to a protein encoding sequence. The promoter includes a nucleotide sequence having a homology ranging upwards of 80% with a sequence upstream from residue −348 (residues 1343 in SEQ ID NO: 1) in FIG. 1. A preferred construct includes a nucleotide sequence substantially identical with the sequence from about residue −1044 to residue −348 from about residue 647 to about residue 1343 in SEQ ID NO: 1).

In a further aspect of the invention, a cell line is transfected with a DNA construct of the invention. Preferably, the cell line is selected from thyroid tissues. A particularly preferred cell line is KAT-50, which is a thyroid cell line.

A method for promoting expression of a protein in vitro is also contemplated. Such method comprises transfecting a cell line with a DNA construct comprising an hNIS promoter of the invention operatively linked to a nucleotide sequence encoding the protein, and incubating the cell line under biological culture conditions.

A particularly notable aspect of the invention pertains to its use in diagnostic assays for a defective hNIS promoter present in the genome of a person. A defective promoter, having one or more mutations or deletions from the reported sequence, can be probed using one or more oligonucleotides based on the nucleotide sequence shown in FIG. 1. This assay entails probing for defects and/or mutations in the hNIS promoter by amplifying part or all of the sequence between residues −1690 to −348 (residues 1 to 1343 in SEQ ID NO: 1) and identifying the amplified product.

A related assay can be used to probe whether the promoter is likely methylated, which shuts off hNIS gene expression.

Preferred oligonucleotides for use in such an assay are inclusive of DNA sequences identical or complementary to portions of a CG-containing sequence between about residue −850 and residue −348 in FIG. 1 (about residue 841 and residue 1343 in SEQ ID NO: 1). Low levels of hNIS expression have implications for thyroid function and for radioiodide treatment of thyroid cancer.

DESCRIPTION OF THE FIGURES

FIG. 1 depicts the nucleotide sequence of the hNIS promoter region. Upper-case letters indicate translated sequences and numbering of sequences is relative to the translation start site. Thin arrows denote the boundaries of the promoter portions of the chimeric transfection constructs with the unlabeled arrow showing the common 3' end (position −336) (position 1355 in SEQ ID NO: 1). Thin arrows A, B, and C represent the 5' ends of these respective promoter portions (Constructs: A at −930 (posistion 761 in SEQ ID NO: 1), B at −1044 (position 647 in SEQ ID NO: 1), C at −1108 (position 583 in SEQ ID NO: 1). Putative transcription factor binding sites are underlined as: TTF1 (thin line), TTF2 (thick line), and PAX-8 (broken line). The 5' ends of the cDNA clone of Smanik et al (2) (thick SJ arrow) and three of our clones (thick VA1 arrow, one clone, and thick VA2 arrow, two clones) are marked as indicated.

DETAILED DESCRIPTION OF THE INVENTION

Figure 2:
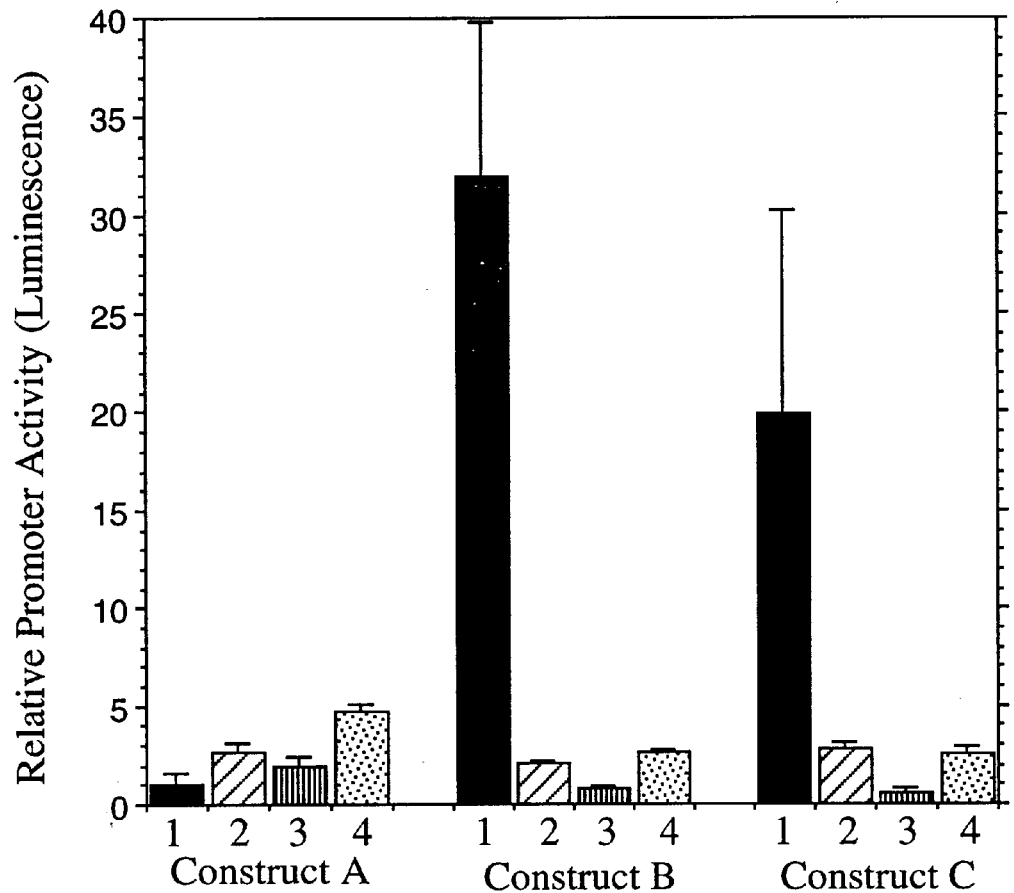
FIG. 2 depicts cell line-specific activity of different hNIS promoter fragments. Luciferase activity, as a measure of promoter strength, is expressed as relative luminescence units (mean± SEM of 3–8 replicates for each condition). Three different chimeric hNIS promoter-luciferase reporter constructs (A, B, C; as described herein) were transfected into four distinct cell lines. The human differentiated thyroid cell line, KAT-50, (#1), two other human non-thyroid cell lines (HeLa, #2 and Hep G2, #3), as well as a simian cell line (COS-1, #4) were evaluated activity of each promoter construct. All values are normalized relative to the activity of the promoter-less luciferase gene vector (NC, pGL3-basic) in each respective cell line. The normalized positive control vector activities (mean±SEM) were: KAT-50 (456±97); HeLa (159±11); Hep G2 (306±21); and COS-1 (1074±16).

As described more fully hereinbelow, the nucleotide sequence shown in FIG. 1 (SEQ ID NO: 1) includes the minimal essential promoter for the hNIS gene. It is contemplated that the hNIS promoter, either in its entirety or by selection of essential fragments thereof, can facilitate expression of an hNIS coding region or other nucleotide sequence heterologous to the hNIS promoter. Accordingly, a promoter, or effective fragment thereof, for the human sodium-iodide symporter is defined within the nucleotide sequence shown in FIG. 1. Expression of the gene under control of the hNIS promoter or fragment thereof can take place in a variety of cell types, most preferably in thyroid cell lines.

An hNIS promoter or promoter fragment of the invention has a high degree of homology with the hNIS promoter sequence shown in FIG. 1. It is preferred that the promoter or promoter fragment is at least 80% homologous, more preferably at least 90% homologous, with a nucleotide sequence shown in FIG. 1. As shown herein, a preferred nucleotide sequence of FIG. 1 defining the minimum essential promoter of the hNIS gene is set forth from about residue −1044 (position 647 in SEQ ID NO: 1) to about residue −348 (position 1343 in SEQ ID NO: 1). Moreover, a nucleotide sequence containing the sequence from −1108 to −1040 posistion 651 in SEQ ID NO: 1 and further inclusive of the sequence from −1040 to −348 (position 1334 to position 651 in SEQ ID NO: 1) is found to have comparable activity. Consequently, a DNA molecule containing a sequence homologous with the sequence extending from residue −1040 to residue −348 (residue 651 to residue 1343 in SEQ ID NO: 1), such as one including the sequence extending from −1108 to −348 (position 583 to position 1343 SEQ ID NO: 1), is a promoter of the present invention.

The percentage of "homology," as used herein, refers to the extent to which a nucleotide sequence maps into the minimum essential promoter of the hNIS gene. In making this comparison, deletions, substitutions, mutations, repeats, and the like, of the subject promoter must be compared with the now known nucleotide sequence of the hNIS promoter. The ratio of identical nucleotides, after taking into account any of the above alterations, determines the extent of homology between the subject sequence and the hNIS promoter. Particularly preferred methods of determining the degree of homology are well known and are described, for instance, by Altschul, S. et al. (1990) *J.Mol. Biol.*, 215:403–410 and Karlin, S. et al. (1993) *PNAS USA*, 90:5873–5877.

In a preferred embodiment, a promoter of the invention contains TTF1, TTF2 and PAX-8 transcription factor binding sites. Additionally, one or more Sp1 transcription factor binding sites, such as those upstream of residue −348 (residue 1343 in SEQ ID NO: 1), can be present. One such promoter is defined substantially by the nucleotide sequence shown in FIG. 1 from residue −1044 to residue −348 (residue 647 to residue 1343 in SEQ ID NO: 1). Hence, a preferred promoter is one having a high degree of homology, preferably at least 80% and more preferably at least 90%, with this sequence. Particularly preferred is a promoter having a nucleotide sequence substantially identical with that shown in FIG. 1 from residue −1044 to residue −348 (residue 1343 in SEQ ID NO: 1) (residue 647 to residue 1343 in SEQ ID NO: 1). A still more particularly preferred promoter has a nucleotide sequence substantially identical with that from about residue −1690 to residue −348 (residue 1 to residue 1343 in SEQ ID NO: 1).

A DNA construct, such as an expression vector, is also contemplated within the invention. Such a DNA construct comprises a promoter sequence of the invention operably linked to a protein encoding sequence. The promoter includes a nucleotide sequence having a degree of homology upwards of 80% when compared with a sequence upstream from about residue −348 (residue 1343 in SEQ ID NO: 1) in FIG. 1, as described above. A preferred construct includes the nucleotide sequence from about residue −1040 to residue −348 (resisdue 615 to redidue 1343 in SEQ ID NO: 1). A further preferred construct includes the nucleotide sequence from residue −1108 to residue −348 (residue 583 to residue 1343 in SEQ ID NO: 1). The protein encoding sequence may be one that encodes the hNIS protein, such as whenever it is desired to increase expression of this protein in a cell, e.g., a carcinoma. Alternatively, the protein encoding sequence may be heterologous to the promoter, i.e., it may be a coding sequence that is not ordinarily under the control of the hNIS promoter.

In a further aspect of the invention, a cell line is transfected with a DNA construct of the invention as described hereinabove. Preferably the cell line is from thyroid. A particularly preferred cell line is KAT-50, which is a thyroid cell line, in order that any thyroid-specific effects required for expression are provided.

A method for promoting expression of a protein in a cell, e.g., in vitro, is also contemplated. Such method comprises transfecting a suitable cell line with a DNA construct comprising an hNIS promoter that is operatively linked to a nucleotide sequence encoding the protein. The cell line is then incubated under biological culture conditions to express the desired protein. Preferred cell lines are those mentioned above.

A particularly notable aspect of the invention pertains to its use in a diagnostic assay for a defective hNIS promoter that may be present in the genome of a human. A defective promoter, having one or more mutations or deletions from the correct sequence, can be probed using an oligonucleotide corresponding to the nucleotide sequence shown in FIG. 1. The assay can be used to probe whether the promoter is likely methylated, which prevents or reduces hNIS gene expression. Low levels of hNIS expression have implications for thyroid function and for radioiodide treatment of thyroid cancer.

Oligonucleotides (oligos) for use with this assay typically have a high degree of homology with the sequence −1690 to −348 shown in FIG. 1 (sequence 1 to 1343 in SEQ ID NO: 1), and preferred oligos are substantially identical or complementary to all or a portion of this sequence. An oligo of the invention can include a DNA sequence identical or complementary to a region from about −850 to −348 (about 1343 to 841 to in SEQ ID NO: 1). Particularly preferred oligos are entirely identical or complementary to the CG-rich region between about residue −850 and residue −348 (about 1343 to 841 in SEQ ID NO: 1) It is generally preferred that the oligos are labeled with a chromophore, fluorophore, radiolabel, or other identifying conjugate (e.g., by conjugating a label to the oligo, in order to enhance visualization of hybridization), or are spatially segregated so as to identify complementary sequences. Preferably, an oligo is at least 15, more preferably 20 up to about 100 nucleotides in length. An oligonucleotide can be synthesized readily using known techniques, such as the phosphotriester method [see, e.g., Itakura, K., et al., (1984), *Ann.Rev.Biochem*, 53: 323–356].

A diagnostic screening assay of the invention entails contacting at least one, preferably two, of the aforementioned oligos with the genomic DNA of the human, and subjecting this combination to hybridization conditions effective to detect deletions and/or mutations. Suitable hybridization protocols are well known to those skilled in the art. See, e.g., Sambrook, J. et al., 1989, *Molecular Cloning. A Laboratory Manual*, Cold Spring Harbor Laboratory, as well as more recent modifications of these techniques known to those skilled in the art. The occurrence of any hybridization between the oligo and DNA is then determined, whereby if hybridization occurs, the DNA likely does not have a defective promoter. If hybridization does not occur under these conditions, the presence of a defective promoter is indicated. The above hybridization is preferably performed as part of a PCR protocol, whereby the genomic DNA is effectively amplified, which facilitates its isolation and/or identification.

A diagnostic assay of the invention can provide still further information using the readily available techniques of PCR amplification and DNA sequencing. The primer molecules preferably have a nucleotide sequence identical or complementary to a sequence of FIG. 1 from residue −1690 to −348 (1 to 1343 in SEQ ID NO: 1). It should be appreciated, however, that nucleotide sequences flanking this region, i.e., upstream of −1690 and downstream of −348 (upstream of 1 and downstream of 1343 in SEQ ID NO: 1), can be used to amplify the promoter region, as long as they are effective in amplifying a region within the −1690 to −348 (1 to 1343 in SEQ ID NO: 1) sequence. Of course, the primer molecules must also hybridize with a region of the genomic DNA proximate, if not within, the promoter region of the DNA. PCR amplification is then conducted, e.g., using commercially available equipment and protocols, whereby repeated cycles of hybridization, elongation of the primer chain, and thermal melting are performed in order to amplify a portion or the entirety of the promoter region of the DNA. The amplified product can then be sequenced, e.g., with commercially available equipment and protocols, to identify a mutation or deletion occurring in the genomic DNA.

As described herein, the cloning and functional characterization of the hNIS gene promoter, as well as the demonstration of native expression of this gene in diverse human tissues and a human thyroid cell line has been achieved. To elucidate the role of the promoter in tissue-specific hNIS expression, the activity of chimeric promoter constructs in human thyroid and non-thyroidal cells was evaluated.

The invention is described hereinbelow in more detail with reference to certain examples, which are offered to further explain the invention, but which do not limit it.

EXAMPLE 1

Cell Lines and Human Tissues

KAT-50 (available from our lab) is a cell line established by primary culture from the thyroid of a 3 year-old boy with benign follicular hyperplasia. This cell line was used to demonstrate thyroid-specific promoter activity, since this is the only known human thyroid cell line which retains functional NIS expression and iodide-concentrating activity in vitro (available from our lab). Cultures were treated for 4 wks in media containing D-valine (4) and cis-4-hydroxy-L-proline (5) to ensure elimination of fibroblasts. Other human thyroid cell lines were: ARO81 and DRO90 (both from anaplastic carcinomas, provided by G. J. F. Juillard, Univ. of California-Los Angeles School of Medicine), BHT-101 (anaplastic carcinoma, provided by I. Palyi, National Institute of Oncology, Budapest, Hungary) (6), KAT-4 and KAT-18 (anaplastic carcinomas, from our lab) (7), NPA 87 (papillary carcinoma, from Juillard), KAT-5 and KAT-10 (8) (both papillary carcinomas, from our lab), KAK-1 (benign follicular adenoma, from our lab) (9), KAT-7 (benign follicular hyperplasia, from our lab), and KAT-9 (derived from Hashimoto's thyroiditis-afflicted follicular cells, from our lab). Additional cell lines include: HeLa, human epithelial cervical carcinoma; Hep G2, human hepatoma; and COS-1, SV-40-transformed African green monkey kidney cells. All of the thyroid-derived cell lines were grown in RPMI 1640 with 10% fetal bovine serum (FBS), with the other cell lines grown in DMEM/F12 (1:1) with 10% FBS (all from Life Technologies, Gaithersburg, Md.). Normal human tissues were obtained from fresh surgical samples.

EXAMPLE 2

Nucleic Acid Isolation and Amplification (RT-PCR)

RNAs from normal tissues and cell lines were isolated by the acid-guanidinium-phenol-chloroform method (10). Complementary DNA (cDNA) was synthesized from 0.5 $\mu$g of total RNA using MMLV reverse transcriptase (RT) with random-hexamer primers (Clontech, Palo Alto, Calif.). Each 50 $\mu$L polymerase chain reaction (PCR) contained 60 mM Tris HCl, pH 9.0, 15 mM ammonium sulfate, 3.5 mM MgCl$_2$ (for PAX-8 at 2 mM), 250 $\mu$M dNTPs, 2 $\mu$M primers, 1 U AmpliTaq DNA polymerase (Perkin-Elmer, Norwalk, Conn.), 0.2 μg TaqStart Antibody (Clontech) and 1% cDNA. β-actin amplification (primers, Stratagene, La Jolla, Calif.) confirmed cDNA integrity, purity, and template equivalence. PCR primers and product sizes are (upstream 5' to 3'/downstream 5' to 3'):

TG (thyroglobulin, 174 bp):
AACTTCAGTCTCTTTATTCAAAGTCTC (SEQ ID NO. 2)
GCCATTTAAGATCTGCCAGAAGAG (SEQ ID NO: 3)
TPO (thyroid peroxidase, 472/342 bp, splice variant):
CCCCTACGAGTTAGGAGACGATGC (SEQ ID NO: 4)
CATCCATGCCTGAGAGTAACTACG (SEQ ID NO: 5)
TSH-R (thyrotropin receptor, 367 bp):
GGGTGCAACACGGCTGGTTT (SEQ ID NO: 6)
CTGGGTTGTGCGGATTTCGG (SEQ ID NO: 7)
TTF1 (thyroid transcription factor-1, 257 bp):
CGCCGTACCAGGACACCATGAGC (SEQ ID NO: 8)
GACAGGTACTTCTGTTGCTTGAAG (SEQ ID NO: 9)
PAX-8 (329 bp):
CACAAGTCCAGCATTGCGGCACATC (SEQ ID NO: 10)
CTGGAGGGAAGTGCTGCTTATGGTCC (SEQ ID NO: 11)
hNIS (303 bp):
CTGCCCCAGACCAGTACATGCC (SEQ ID NO: 12)
TGACGGTGAAGGAGCCCTGAAG (SEQ ID NO: 13).

The hNIS primers amplify a region of the hNIS gene spanning four introns (3) to yield the 303 bp product with cDNA only and will not amplify genomic DNA. Amplification conditions are: denaturation 94° C.×3 min; 40 cycles of 20 sec at 94° C., 30 sec at 62° C. (64° C. for hNIS) and 60 sec at 72° C.; followed by 72° C. for 7 min.

EXAMPLE 3

Iodide Uptake in KAT-50 Cells

KAT-50 cells (1×10$^5$/9.4 cm$^2$) were grown in phenol red-free RPMI 1640 with 10% FBS (±0.1 NM bTSH), in 6 well plates. Medium was replenished on the 4th day. At the end of 7 days, cells in each well were washed with 2 mL of buffer, containing: 10 mM HEPES, pH 8.3 (with 5.5 mM glucose, 5.4 mM KCl, 1.3 mM CaCl$_2$, 0.4 mM Na$_2$HPO$_4$, and 0.44 mM KH$_2$PO$_4$), and either 137 mM NaCl (Buffer A) or 100 mM choline chloride (Buffer B). After incubation in the same volume of the same buffer, supplemented with Na[$^{125}$I](1.0 μCi/2 mL) and 1.0 μM NaI, for 60 min, cells were briefly washed once with Buffer A, trypsinized. and gamma-counted. Trichloroacetic acid (10% v/v) was then added, the contents centrifuged and the pellet resuspended. Pellets, dried at 60° C., were weighed to normalize counts for cell mass.

EXAMPLE 4

Cloning and Sequencing of NIS cDNA

Multiple sets of degenerate oligonucleotide primers, based on the rat NIS cDNA sequence (1), were used to amplify fragments of hNIS cDNA from random-hexamer-primed human thyroid cDNA. Two major amplification products were sequenced and additional primers were synthesized and used for further RT-PCR amplifications to obtain 1.6 kb of hNIS cDNA sequence. From this, a 5'-proximal α-$^{32}$P-labeled DNA probe was synthesized and used to screen a human thyroid cDNA library (kindly provided by Basil Rapoport, VAMC, San Francisco, Calif.). Twelve different positive cDNA clones were obtained, analyzed by restriction enzyme digestion with electrophoresis on agarose gels, and the three clones containing the longest upstream extent of hNIS gene were sequenced.

EXAMPLE 5

Cloning and Sequencing of the Promoter

The upstream regulatory region of the NIS was cloned using the PromoterFinder™ DNA walking kit (Clontech) with a combination of Tth (Epicenter Tech., Madison, Wis.) and Vent (New Eng. BioLabs, Beverly, Mass.) DNA polymerases for long distance PCR reaction (11). This kit contains five "libraries" that are pools of DNA fragments obtained from digestion of genomic DNA derived from human placenta, ligated to a proprietary DNA adapter which provides a PCR priming site. The first round of PCR used gene specific primer (GSP-1) (5'–3'): CCACGGCCTCCAT-GAGGGCGGGTGCGGA (SEQ ID NO: 14) and commercial adapter-primer-1. The gene-specific primers were chosen to be near the 5'-most end of our three cDNA clones (see prior section). The second PCR round used GSP-2: TAG-GAATCTATGGGCTGTCGATGTCCGT (SEQ ID NO: 15) and commercial adapter-primer-2, These PCR products (and plasmid DNA when applicable) were sequenced by fluorescence dye-terminator method (Model 373A, Perkin Elmer Applied Biosystems, Foster City, Calif.) at the Macromolecular Structure Analysis Facility, University of Kentucky. Promoter fragments were sequenced in both directions using synthetic oligonucleotide primers.

EXAMPLE 6

5' Rapid Amplification of c-DNA Ends (5'-RACE) to Define Transcription Start Site The transcription start site was mapped by a modification of the 5'-RACE (Rapid Amplification Capillary Electrophoresis) method of Frohman (12), using human thyroid cDNA ligated to a commercial adapter (Marathon-Ready® cDNA, Clontech). Antisense primers (GSP-2; and RX1, GCTGGTGAGGCCCAGGCGGT (SEQ ID NO: 16) were used in combination with the sense adapter-primer in two separate PCR amplifications of the human thyroid cDNA. The lengths of these products were aligned to the corresponding cDNA sequence map and compared to the ends of the cDNA clones obtained screening the human thyroid cDNA library from Dr. Rapoport. In separate experiments, PCR amplifications using different sense primers, corresponding to DNA regions upstream of the putative transcription start site were performed in combination with either the GSP-2 or GSP-1 antisense priming sequences.

EXAMPLE 7

Vector Constructions and Transfection

Chimeric promoter-Luciferase reporter constructs were made by incorporating amplified promoter fragments in the promoter-less pGL3-Basic vector (Promega, Madison, Wis.), as follows: A, −930 to −336; B, −1044 to −336; and C, −1108 to −336. The recombinant constructs were sequenced for verification. The negative control (NC) is the pGL3-Basic vector alone and the positive control (PC) is the pGL3-Control vector with an SV-40 enhancer and promoter.

Specific promoter fragments were generated by high fidelity-PCR using primers introducing KpnI (5') and XhoI (3') restriction sites bracketing the promoter regions. KAT-50 ($1\times10^6$ cells/9 cm$^2$ well), HeLa ($4\times10^5$), HepG2 ($2\times10^5$) and COS-1 ($2\times10^5$) were transiently transfected, after 24 hrs, with 1.0 µg plasmid DNA/0.625 µg lipofectamine complex in serum-free and phenol red-free medium. After five hrs, medium was replaced and cultures incubated for 48 hrs at 37° C., in 5% $CO_2$. Luciferase activity was measured using commercial Reporter Lysis Buffer and the Luciferase Assay Substrate (both from Promega) on a microtiter plate luminometer (Model ML 2250, Dynatech Laboratories, Chantilly, Va.).

Results

Cloning of the hNIS cDNA and Location of Transcription Start Site

We sequenced the cDNA for the hNIS coding region and verified that it replicated the published sequence of Smanik et al. (2) with the addition of further upstream coding sequences as indicated in FIG. 1. Our 5' RACE analysis of the adapter ligated human thyroid cDNA, with the adapter primer and two different downstream antisense primers (GSP2 and RX1) generated products of approximately 250 bp and 750 bp, respectively. This localized the transcription initiation site to the same region as the 5'-end of our longest cDNA clones (FIG. 1, VA1 and VA2 arrows). The upstream primers used for the generation of the transfection constructs (and one other primer, spanning −783 to −762) (908 to 929 in SEQ ID NO: 1), used with GSP1 or GSP2 as the downstream primers, were unable to amplify any RT-PCR product from human thyroid cDNA, indicating the absence of coding sequences immediately upstream (by at least 750 bp) of our putative transcription start site.

Cloning of the hNIS Promoter and Sequence Analysis

We sequenced 1.2 kb of the non-transcribed genomic region upstream of the hNIS cDNA (FIG. 1). Analysis of the 1.5 kb region upstream of the translation start codon reveals the absence of typical TATA box elements. Two CAAT boxes are located at −405 and −1105 (1356 and 586 in SEQ ID NO: 1). A TATA-like AT-rich sequence, AATAAATCT (−404 to −396) (1657 to 1295 in SEQ ID NO: 1) (SEQ ID NO: 17 overlaps with the proximal CAAT element. As shown in FIG. 1, this region is highly GC-rich (nucleotides −1 to −900) (1750 to 600 in SEQ ID NO: 1) and contains putative binding sites for thyroid associated transcription factors: TTF1 (at −710, −720, −916 & −925, 276, 288, 806 and 815 in SEQ ID NO: 1) (13, 14); PAX-8 (at −376, −451, −550 & −656, 1315, 1241, 1100 and 1086 in SEQ ID NO: 1) (14, 15); and TTF2 (at −762 & −844) (929 and 794 in SEQ ID NO: 1) (16). There are also multiple potential binding sites for the transcription factor, Sp1 (at −9, −93, −242, −270, −434, −449, −537 & −861, 1681, 1603, 1392, 1420, 1224, 1239, 1164 and 2940 in SEQ ID NO: 1) (17). An unusual region of repeated GAAT units spans −1110 to −1057. In addition, a 14-nucleotide direct repeat element, GTGCATGGGGATGG (SEQ ID NO: 18), separated by four bases, spans positions −574 to −561 and −566 to −553. A repeat element of the Alu family is found upstream of −150). Sequences of the Alu family are exclusively found in humans and other primates [Mighell, A., et al. (1997), FEBS Lett., 417:1–5].

Characterization of KAT-50 Cell Line

KAT-50 demonstrates log-phase growth at a doubling time of 36 hours. RT-PCR analysis of this human thyroid cell line, for the expression of mRNAs for hNIS, TG, TPO, TSH-R, and transcription factors (TTF1 and PAX-8), revealed distinct expression of all of them. Analysis of 12 other cell line monolayers revealed hNIS expression in 4 of 5 anaplastic carcinoma cell lines, but no expression in: 3 papillary carcinoma cell lines, one derived from Hashimoto's thyroiditis-affected follicular cells, one cell line from a benign follicular adenoma, and another from a gland with benign follicular hyperplasia.

The results of studies in our lab indicated that KAT-50 cells in basal medium have minimal iodide uptake when non-specific activity (represented by choline-treated KAT-50 cells) is subtracted. Bovine TSH administration for 7 days augments iodide uptake in KAT-50 cell monolayers by more than 3-fold (approximately 3000 cpm/well compared with 1000 cpm/well for basal medium). In these studies, radioiodine ($Na[^{125}I]$) uptake in KAT-50 cells was measured in basal medium and following thyrotropin (TSH) treatment. KAT-50 cells in choline-containing medium (which blocks transport activity) served as a negative control for radioiodide uptake to account for non-specific binding of tracer. Equal cell numbers in 12 replicate wells for each condition were assayed as described and plotted as mean radioactivity ± SEM. Basal medium was phenol red-free RPMI 1640 with 10% FBS and treatment additive was 0.1 nM bovine TSH.

hNIS Promoter Activity in KAT-50 Cells

Chimeric luciferase reporter constructs were transfected into KAT-50 cells since they express functional hNIS mRNA and have significant iodide-transport ability, denoting an adequate cellular milieu for demonstration of hNIS promoter activity. As shown in FIG. 2, construct A lacked any promoter activity and was comparable to the promoter-less construct (NC), while the constructs B and C conferred a 19- to 32-fold increase in promoter activity.

Thyroid-Specific Expression of hNIS mRNA

The expression of hNIS mRNA in various human tissues by RT-PCR also were evaluated. Thyroid tissues, salivary gland, omentum, and gallbladder were positive for expression of the expected size PCR product. Negative tissues (by ethidium bromide staining) were: prostate, spleen, heart, placenta, uterus, ovary, and non-lactating breast.

Cell-Specific Activity of the hNIS Promoter

To determine whether the active hNIS promoter region, as delineated in KAT-50 cells, is thyroid follicular cell-specific, we measured expression of the same chimeric constructs in non-thyroidal human cell lines as well as a simian cell line (FIG. 2). Luciferase activities of these constructs in each respective cell type were normalized to that of the promoter-less construct in the same cell line. Constructs B and C showed less than 3-fold increased activity in HeLa, Hep G2 and COS-1cell lines, which was much less than the 19- to 32-fold increase observed in KAT-50 cells. In contrast, Construct A, which has no appreciable promoter activity in KAT-50 cells, exhibited a moderate, 2- to 5-fold increase in HeLa, Hep G2 and COS-1 cells. Co-transfections of KAT-50 cells with separate plasmids containing luciferase and β-galactosidase reporter genes, under the control of an SV40 promoter and enhancer, revealed greatly diminished reporter gene activities consequent to interference, in a similar fashion as reported by Farr and Roman (18).

Discussion

These results indicate successful identification of the hNIS gene promoter as well as delineation of a minimal essential regulatory sequence, which confers both promoter activity in differentiated human thyroid cells and cell-type specificity. Thyroid-specific transcription factors (TTF1, TTF2, and PAX-8) have been associated with thyroid-specific gene expression for TG, TSH-R, and TPO in numerous species. Although Construct A contains potential binding motifs for each of these transcription factors, this is not sufficient for promoter activity in KAT-50 thyroid cells and requires the participation of an additional 115 bp upstream for activity of the chimeric constructs. We have not yet identified the role of these motifs in this region to account for this effect. The addition of 65 bp upstream of Construct B, including the GAAT repeat region and the distal CAAT box (constituting Construct C) does not evoke additional luciferase activity in our expression system.

Our independent analysis of the hNIS cDNA sequence was the same as reported by Smanik et al. (2), with the exception of a longer untranslated upstream region. This result, in conjunction with the results of our 5'RACE analysis located the putative transcription start site at least 15 bp upstream of the previously reported sequence. The relative positions of the TATA-like sequence, the CAAT-box, and the Sp1 sites to this start site are in agreement with their consensus positions noted in the majority of vertebrate gene promoters (19).

The KAT-50 cell line is an important research tool for the characterization of iodide transport in human thyroid cells. Because of its expression of the full repertoire of known thyroid-specific genes, its functional expression of hNIS, as well as its demonstrated response to thyrotropin, it should prove to be as relevant to the study of human thyrocyte biology as the FRTL-5 cell line has been for the study of rat thyrocyte biology (20).

RT-PCR for hNIS mRNA in 12 human thyroid cell lines revealed expression of an appropriate-size product in 4 of 5 anaplastic thyroid carcinoma cell lines. This is unexpected, considering the invariable failure of anaplastic tumors to concentrate iodide in their human hosts. It is possible that this expressed hNIS mRNA is mutated or otherwise defective consequent to splicing. Evaluation of iodide uptake in these particular cell lines will be necessary to determine if this is associated with functional expression of symporter protein. Smanik et al. (3) have demonstrated low and variable expression of hNIS mRNA in primary papillary carcinoma tissues while we were unable to see such expression in three such cell lines. It is unclear whether this is related to non-expression in the original parent tumors or consequent to derivation of the cell lines or in vitro conditions.

In addition to expression of hNIS in normal human thyroid tissues, we detected distinct expression in salivary gland, omentum, and gallbladder. Smanik et al (3) have also noted extrathyroidal expression in breast, colon, and ovary. We have not been able to detect hNIS mRNA from human breast or ovary by ethidium bromide staining. Clinically, patients subjected to radioiodine scanning demonstrate extra-thyroidal uptake in salivary glands, gastric mucosa, and intestines, with variable uptake in mammary tissues. The expression of hNIS in gallbladder is not unexpected since this organ develops as an evagination of the embryonic gut (21) and can concentrate radioiodine in diagnostic scanning (22). Although clinical evidence of radioiodine uptake in human omentum has not been reported, it would be difficult to discern from background gut activity and is reasonable to expect since omentum derives from the embryonic mesogastrium (21).

Loss of hNIS expression in metastatic thyroid carcinoma creates a therapeutic dilemma since this renders radioiodine treatment ineffective and active systemic chemotherapies have not been found for this disease. Recent studies in vitro (23) and in vivo (24) suggest that loss of iodide transport is reversible with chemical agents, implying the absence of inactivating mutations. Further investigations of hNIS gene regulation may elucidate the cause of loss of its activity and provide an approach to restore iodide transport.

References

The pertinent portions of the following references are incorporated herein by reference.

1. Dai G. et al., (1996) "Cloning and characterization of the thyroid iodide transporter," *Nature* 379:458–459.

2. Smanik P. et al. (1996) "Cloning of the human sodium iodide symporter," *Biochem Biophys Res Comm* 226:339–345.

3. Smanik P. et al., (1997) "Expression, exon-intron organization, and chromosome mapping of the human sodium iodide symporter," *Endocrinol* 138(8):3555–3558.

4. Gilbert S. et al., (1975) "D-Valine as a selective agent for normal human and rodent epithelial cells in culture," *Cell* 5:11–17.

5. Kao WW-Y. et al., (1977) "Proline analogue removes fibroblasts from cultured mixed cell populations," *Nature* 266:63–64.

6. Palyi I. et al., (1993) "Establishment, characterization and drug sensitivity of a new anaplastic thyroid carcinoma cell line (BHT-101), " *Virchows Archiv B Cell Pathol* 63:263–269.

7. Ain K. et al., (1996) "Antineoplastic activity of taxol against human anaplastic thyroid carcinoma cell lines in vitro and in vivo," *J Clin Endocrinol Metab* 81(10): 3650–3653.

8. Ain K. et al., (1997) "Somatostatin receptor subtype expression in human thyroid and thyroid carcinoma cell lines," *J Clin Endocrinol Metab* 82(6): 1857–1862.

9. Ain K. et al., (1994), "Somatostatin analogs affect proliferation of human thyroid carcinoma cell lines in vitro," *J Clin Endocrinol Metab* 78(5):1097–1102.

10. Chomczynski P. et al., (1987), "Single step method of RNA isolation by acid guanidinium thiocyanate-phenol-chloroform extraction," *Anal Biochem* 162:156–159.

11. Cheng S. et al., (1994), "Effective amplification of long targets from cloned inserts and human genomic DNA," *Proc Natl Acad Sci USA* 91(12):5695–5699.

12. Frohman M. (1993), "Rapid amplification of complementary DNA ends for generation of full-length complementary DNAs: thermal RACE," *Methods Enzymol* 218:340–356.

13. Civitareale D. et al., (1989), "A thyroid-specific nuclear protein essential for tissue-specific expression of the thyroglobulin promoter," *EMBO J* 8(9):2537–2542.

14. Civitariale D. et al., (1993) "Thyroid transcription factor 1 activates the promoter of the thyrotropin receptor gene," *Mol Endocrinol* 7(12):1589–1595.

15. Francis-Lang H. et al., (1992), "Multiple mechanisms of interference between transformation and differentiation in thyroid cells," *Mol Cell Biol* 12(12):5793–5800.

16. Santisteban P. et al., (1992), "Insulin and insulin-like growth factor I regulate a thyroid-specific nuclear protein that binds to the thyroglobulin promoter," *Mol Endocrinol* 6(8):1310–1317.

17. Kadonaga J. et al., (1988), *Science* 242:1566–1570.

18. Farr A. et al., (1992), "A pitfall of using a second plasmid to determine transfection efficiency," *Nucleic Acids Res* 20(4):920.

19. Bucher P. (1990), "Weight matrix descriptions of four eukaryotic RNA polymerase II promoter elements derived from 502 unrelated promoter sequences," *J Mol Biol* 212 (4):563–578.

20. Bidey S. et al., (1988), "Thyroid cell growth, differentiation and function in the FRTL-5 cell line: a survey," *J Endocrinol* 119:365–376.

21. Corliss C. Patten's Human Embryology: Elements of clinical development. New York: McGraw-Hill Book Co. (1976)

22. Achong D. et al., (1991), "Gallbladder visualization during post-therapy iodine-131 imaging of thyroid carcinoma," *J Nucl Med*, 32(12):2275–2277.

23. Van Herle A. et al., (199), "Effects of 13 cis-retinoic acid on growth and differentiation of human follicular carcinoma cells (UCLA RO 82 W-1) in vitro." *J Clin Endocrinol Metab*, 71(3):755–763.

24. Simon D. et al., (1996), "Redifferentiation therapy of differentiated thyroid carcinoma with retinoic acid: basics and first clinical results," *Exp Clin Endocrinol Diabetes*, 104(Suppl 4):13–15.

25. Tong Q., et al., (1997), "Promoter Characterization of the Rat Na$^+$/I$^-$ Symporter Gene," *Biochem. Biophys. Res. Comm.*, 239: 34–41.

26. Endo T., et al., (1997), "Thyroid Transcription Factor-I Activates the Promoter Activity of Rat Thyroid Na$^+$/I$^-$ Symporter Gene," *Mol.Endocrinol.*, 11(11):1747.

27. Altschul, S. et al. (1990) *J.Mol.Biol.*, 215:403–410

28. Karlin, S. et al. (1993) *PNAS USA*, 90:5873–5877.

29. Mighell, A., et al. (1997), *FEBS Lett.*, 417:1–5.

30. Itakura, K., et al. (1984), "Synthesis and use of synthetic oligonucleotides," *Ann.Rev.Biochem*, 53: 323–356.

31. Sambrook, J. et al., 1989, *Molecular Cloning. A Laboratory Manual*, Cold Spring Harbor Laboratory.

The present invention has been described above in some detail for purposes of clarity and understanding. It should be appreciated, however, that the scope of the invention is defined by the appended claims, and that certain obvious modifications and improvements can be practiced within the scope of these claims and their equivalents.

What is claimed is:

1. A DNA molecule consisting of at least about 15 contiguous nucleotides of SEQ ID NO:1 residues 647–1343 or at most about 696 contiguous nucleotides of SEQ ID NO:1 residues 647–1343.

2. A DNA molecule fully complementary to the DNA molecule of claim 1.

3. The DNA molecule of claim 1 or 2 wherein the DNA molecule comprises a sequence which specifically hybridizes to a nucleic acid molecule comprising SEQ ID NO:1 or a sequence fully complementary thereto to form a detectable target:probe duplex.

4. A DNA molecule as in claim 1 which contains TTF1, TTF2 and PAX-8 transcription factor binding sites.

5. DNA molecule as in claim 4 which further comprises at least one Sp1 site upstream of residue 1343 of SEQ ID NO:1.

6. A DNA construct consisting of at most about 5590 nucleotides and comprising a promoter which promoter comprises the nucleotide sequence of SEQ ID NO:1 residues 647 to 1343 and which promoter is operably linked to a protein encoding sequence.

7. A method comprising:

a) contacting at least one oligonucleotide comprising the DNA molecule of claim 3 with nucleic acid derived from a human thereby forming a hybridization product;

b) identifying the hybridization product.

8. The method of claim 7 wherein said oligonucleotide is labeled.

9. The method of claim 7 further comprising an amplification reaction.

10. The method of claim 8 wherein said amplification reaction is PCR.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1750 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GAGTAGCTGG GATTACAGGC ATGTGCCACC ACGCCTCGCT AATATTAGTA TTTTTCATAC      60

AGACAAGATC TCACTATGTT GCTCAGGGTA GTCTCGAATT CTGGGACTCA AATGATCCTC     120

CCACTTCAGC CTCCCAAAGT GCTGGGATTA CAGGCATAAG CCATCATGCC CGGCCTCTGA     180

CGCTGTTTCT TTCAACCCCC AGGATTTCAG ATTCCACCAG CTTATGGAGA AGGGAACCAA     240

GTTCGAGATG CGTGATTGCC CAGAAAGTTG GAGGCTGAGC TGAGACTTGA ACCCAGAGAC     300

CAGAACCTCC AGAGGTCAAA GTCCTCCTCC TGGGTCCCCC AGAGAAGGGC CCTGAGATGA     360

CAGCTCGTTG GTCCTCATGG AAGCGTGACC CCCCAGTAG ACTTTCTCCC ACACCCAACC      420

TTGGTTTCCT CATCTATATG ATAGGGACAA GCCAGACTCT ACCTCCCTGG TGGTCATGGT     480

CTCCGCTTAT TCGGGTTCAT AACCTTAAAG GCCCCTCGCA CCACCTCAGT GAGCCATTTA     540

TGCCTGGCAC AGGGCCAACT CTCAGTGCAT ATCTGCAAAG GAACCAATGA ATGAGTGAAT     600

GAAGTGACAA ATGAATAAAG GAATAAATGA ATGAGGCACT TATCATGTAC CAGGCTTTCG     660

TTACCACGTC CCATTTATTC CTCTGAGGCA GGGTCTATTT TATCCTTGTT ACAGATGGGG     720

AAACTAAGGC CCAGGGAGGA GCAAAGTCTT CCCCAAGTAT GTACCCACTC AGAACTTGAG     780

CTCTGAATGT CTCCCACCCA GCTTAGCCCA AGAGCGGGGT TCAGTGATGC CCACCCCTA     840

AGGCTCTAGA GAAAGGGGGT AGGCCCACAT GCCAGTTTGG GGGTGGTAAA GCCAGGTAAG     900

TTTTCTTTAT GGGTCCCCTG AAACCCTGAA AGTGAACCCC AGTCCTGCAT GAAAGTGAGC     960

TCCCCATAGC TCAAGGTATT CAAGCACAAT ACGGCTTTGA GTGCTGAAGC AGGCTGTGCA    1020

GGCTTGGATA GTGACATGCC CTCTCTGAGC CTCAATTTCC CCACCTGTCA ACAGCAGACA    1080

GTGACAGCTG TGATCAGGGG ATCACAGTGC ATGGGGATGG GTGGGTGCAT GGGGATGGAG    1140
```

```
GGGCATTTGG GAGCCCTCCC CGATACCACC CCCTGCAGCC ACCCAGATAG CCTGTCCTGG   1200

CCTGTCTGTC CCAGTCCAGG GCTGAAAGGG TGCGGGTCCT GCCCGCCCCT AGGTCTGGAG   1260

GCGGAGTCGC GGTGACCCGG GAGCCCAATA AATCTGCAAC CCACAATCAC GAGCTGCTCC   1320

CGTAAGCCCC AAGGCGACCT CCAGCTGTCA GCGCTGAGCA CAGCGCCCAG GGAGAGGGAC   1380

AGACAGCCGG CTGCATGGGA CAGCGGAACC CAGAGTGAGA GGGGAGGTGG CAGGACAGAC   1440

AGACAGCAGG GGCGGACGCA GAGACAGACA GCGGGACAG GGAGGCCGAC ACGGACATCG    1500

ACAGCCCATA GATTCCTAAC CCAGGGAGCC CCGGCCCCTC TCGCCGCTTC CCACCCCAGA   1560

CGGAGCGGGG ACAGGCTGCC GAGCATCCTC CCACCCGCCC TCCCCGTCCT GCCTCCTCGG   1620

CCCCTGCCAG CTTCCCCCGC TTGAGCACGC AGGGCGTCCG AGGACGCGCT GGGCCTCCGC   1680

ACCCGCCCTC ATGGAGGCCG TGGAGACCGG GGAACGGCCC ACCTTCGGAG CCTGGGACTA   1740

CGGGGTCTTT                                                         1750
```

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
AACTTCAGTC TCTTTATTCA AAGTCTC                                        27
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GCCATTTAAG ATCTGCCAGA AGAG                                           24
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CCCCTACGAG TTAGGAGACG ATGC                                           24
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CATCCATGCC TGAGAGTAAC TACG                                                      24

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGTGCAACA CGGCTGGTTT                                                           20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTGGGTTGTG CGGATTTCGG                                                           20

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGCCGTACCA GGACACCATG AGC                                                       23

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GACAGGTACT TCTGTTGCTT GAAG                                                      24

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CACAAGTCCA GCATTGCGGC ACATC                                                     25

(2) INFORMATION FOR SEQ ID NO:11:
```

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

CTGGAGGGAA GTGCTGCTTA TGGTCC                                          26

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTGCCCCAGA CCAGTACATG CC                                              22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGACGGTGAA GGAGCCCTGA AG                                              22

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCACGGCCTC CATGAGGGCG GGTGCGGA                                        28

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TAGGAATCTA TGGGCTGTCG ATGTCCGT                                        28

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:16:

GCTGGTGAGG CCCAGGCGGT                     20

(2) INFORMATION FOR SEQ ID NO:17:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AATAAATCT                                  9

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTGCATGGGG ATGG                            14